United States Patent
Yu et al.

(10) Patent No.: US 11,141,165 B2
(45) Date of Patent: Oct. 12, 2021

(54) HEMOSTATIC CLAMP

(71) Applicant: BEIJING DONGLIN FUSHI MEDICAL DEVICES CO., LTD., Beijing (CN)

(72) Inventors: Ling Yu, Beijing (CN); Chun Yu, Beijing (CN)

(73) Assignee: BEIJING DONGLIN FUSHI MEDICAL DEVICES CO., LTD., Beijing (CN)

(*) Notice: Subject to any disclaimer, the term of this patent is extended or adjusted under 35 U.S.C. 154(b) by 0 days.

(21) Appl. No.: 16/745,078

(22) Filed: Jan. 16, 2020

(65) Prior Publication Data

US 2021/0137525 A1 May 13, 2021

(30) Foreign Application Priority Data

Nov. 11, 2019 (CN) .......................... 201911094245.4
Nov. 11, 2019 (CN) .......................... 201921932299.9

(51) Int. Cl.
*A61B 17/122* (2006.01)
*A61B 17/128* (2006.01)
*A61B 17/12* (2006.01)

(52) U.S. Cl.
CPC .......... *A61B 17/122* (2013.01); *A61B 17/128* (2013.01); *A61B 2017/12004* (2013.01)

(58) Field of Classification Search
CPC ..... A61B 17/10; A61B 17/122; A61B 17/128; A61B 17/1285; A61B 2017/12004; A61B 2017/2931; A61B 2017/294
See application file for complete search history.

(56) References Cited

U.S. PATENT DOCUMENTS

| 9,456,824 B2 | 10/2016 | Willett et al. |
| 2009/0318937 A1 | 12/2009 | Matsuoka et al. |
| 2018/0153552 A1* | 6/2018 | King ................ A61B 17/12009 |

FOREIGN PATENT DOCUMENTS

| AU | 2004289214 B2 | 5/2005 |
| CN | 205493927 U | 8/2016 |

OTHER PUBLICATIONS

Extended European Search Report from EP app. No. 20151352.0, dated May 19, 2020.

* cited by examiner

*Primary Examiner* — Melanie R Tyson
(74) *Attorney, Agent, or Firm* — Ladas & Parry, LLP (57) ABSTRACT

The present disclosure discloses a hemostatic clamp. Two clamping pieces are opened and closed through a ball head pull rod, and a clamping portion at a front end of the hemostatic clamp and a control portion at a rear end are separated through fit of the ball head pull rod with a plastic sleeve and a steel sleeve. Therefore, the hemostatic clamp has the advantages of simple structure, simple operation and high operation stability.

15 Claims, 8 Drawing Sheets

HEMOSTATIC CLAMP

CROSS-REFERENCE TO RELATED APPLICATIONS

This application claims priority to Chinese Application No. 201911094245.4 filed on Nov. 11, 2019, and Chinese Application No. 201921932299.9 filed on Nov. 11, 2019, the disclosures of which are hereby incorporated by reference in their entireties.

BACKGROUND

Technical Field

The present disclosure is directed to a hemostatic clamp, in particular to a medical hemostatic clamp pulled by a ball head pull rod, and belongs to the technical field of medical instruments.

Related Art

Endoscopic metal clamp hemostasis is one of the widely used hemostasis means. Proficient metal clamp operation on appropriate cases can effectively stop bleeding and prevent rebleeding, reduce adverse reactions, and greatly improve safety and a cure rate of endoscopic treatment of gastrointestinal bleeding. A hemostatic mechanism of a metal hemostatic clamp is the same as that of surgical vessel ligation or suture. It is a physical and mechanical method. By using mechanical force generated when the hemostatic clamp is closed, surrounding tissues and a bleeding blood vessel are ligated together, thereby closing the bleeding blood vessel to block blood flow to achieve the goal of stop bleeding. It is suitable for hemostasis treatment of non-variceal active bleeding and visible vascular stump lesions.

The existing hemostatic clamp has the defect of being difficult to operate, and the hemostatic clamp cannot be tentatively operated. Once it is closed, it cannot be opened again. If there is an operational error, the hemostatic clamps will be directly discarded. Therefore, it is necessary to provide a hemostatic clamp that can be reopened before clamping the tissue and can be locked after clamping the tissue.

In addition, the existing hemostatic clamps mostly use a three-jaw circlip to realize separation between the hemostatic clamp and a control portion, and have the problems of difficulty in separation and the like when in use.

SUMMARY

A technical problem to be solved by the present disclosure is to provide a hemostatic clamp.

In order to achieve the above objective, the present disclosure adopts the following technical solution:

A hemostatic clamp includes a fixed mount, two clamping pieces and a ball head pull rod, the two clamping pieces being oppositely disposed at a front end of the fixed mount, and the ball head pull rod being configured to drive opening and closing of the two clamping pieces.

The hemostatic clamp also includes a plastic sleeve and a steel sleeve, the plastic sleeve and the steel sleeve are disposed on a lower portion of an inner cavity of the fixed mount, the plastic sleeve being disposed between the steel sleeve and an inner wall of the fixed mount.

The ball head pull rod includes a pull rod and the ball head disposed at a front end of the pull rod. The ball head pull rod passes through the steel sleeve.

After the ball head pull rod is separated from the clamping pieces, by pulling the ball head pull rod rearward, the ball head drives the steel sleeve to slide out of the plastic sleeve.

Preferably, an inner surface of the plastic sleeve is an inclined conical surface, and an inner diameter of a top of the plastic sleeve is greater than an inner diameter of a bottom of the plastic sleeve.

A size of the inner surface of the plastic sleeve matches a size of an outer surface of the steel sleeve at a portion fitting therewith.

Preferably, the steel sleeve is divided into upper and lower portions. The upper portion is configured to match the plastic sleeve, and the lower portion is configured to connect a spring tube.

Preferably, an outer surface of the upper portion of the steel sleeve forms an interference fit with an inner surface of the plastic sleeve.

Preferably, a plurality of holes is disposed in circumference of the fixed mount, and the plastic sleeve is bonded to the fixed mount by injecting glue into the fixed mount through the holes.

Preferably, a diameter of the ball head is greater than a diameter of the pull rod, and the diameter of the ball head is greater than an inner diameter of the steel sleeve. The diameter of the pull rod is equal to the inner diameter of the steel sleeve.

Preferably, the ball head pull rod also includes a connecting tube, a top of the connecting tube being connected to the pull rod, and a bottom of the connecting tube being configured to be connected to a pull rope.

According to the hemostatic clamp provided by the present disclosure, the two clamping pieces are opened and closed through the ball head pull rod, and a clamping portion at a front end and a control portion at a rear end are separated through fit of the ball head pull rod with the plastic sleeve and the steel sleeve. Therefore, the hemostatic clamp has the advantages of simple structure, simple operation and high operation stability and is a hemostatic clamp suitable for wide use.

DETAILED DESCRIPTION

The following further describes the technical solutions of the present disclosure with reference to the accompanying drawings and specific embodiments. In the following description, a clamping portion for clamping a blood vessel is a front end, and a control portion of the hemostatic clamp for a doctor to operate is a rear end.

Figure 1:
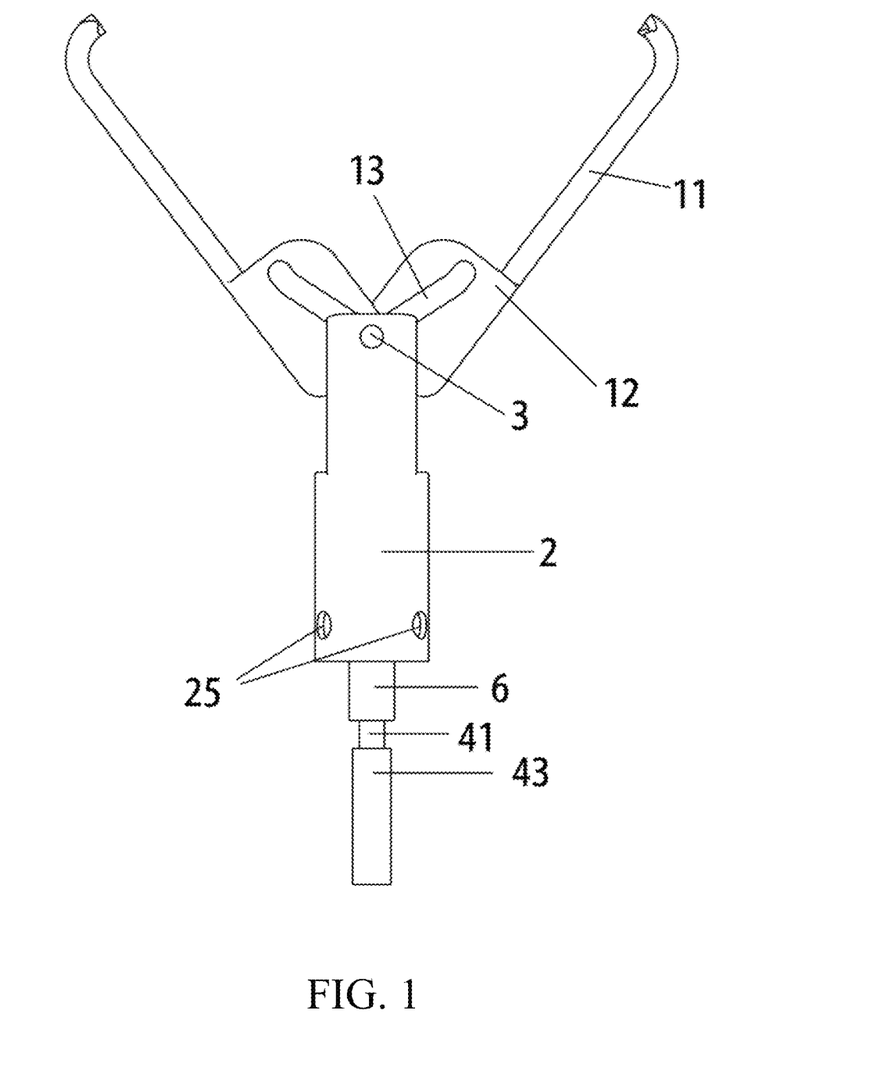
FIG. 1 is a schematic structural diagram of a hemostatic clamp provided by the present disclosure.
Figure 2:
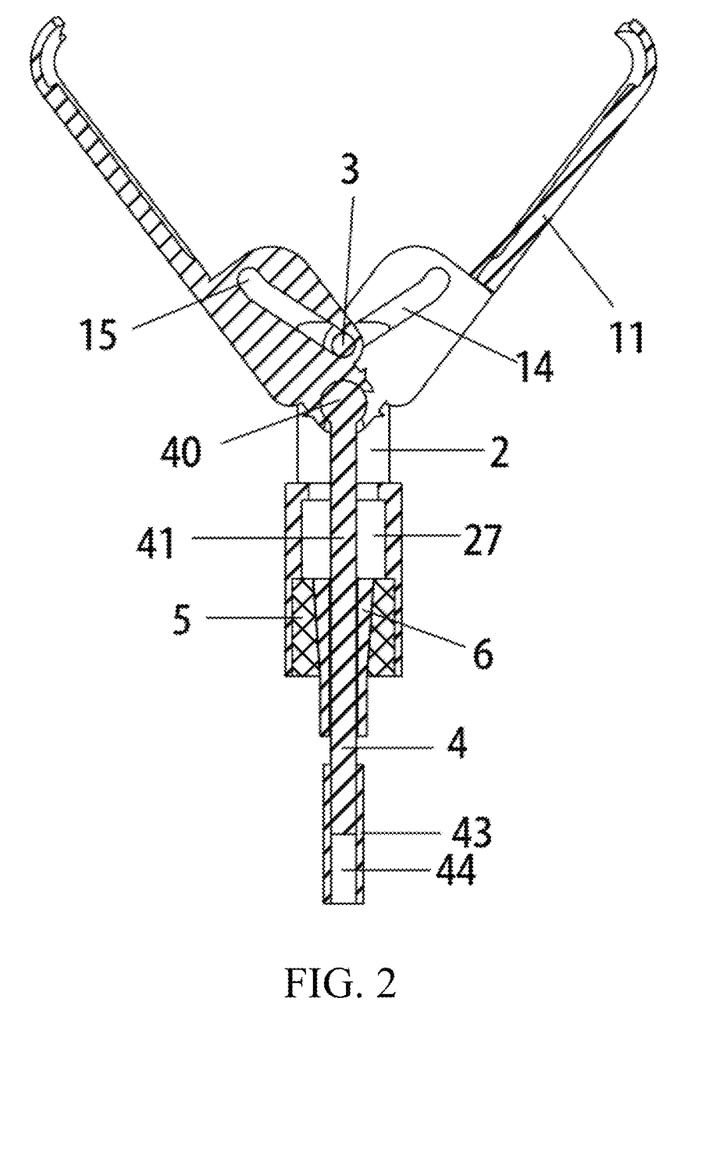
FIG. 2 is a schematic cross-sectional view of the hemostatic clamp shown in FIG. 1.

As shown in FIG. 1 and FIG. 2, the hemostatic clamp provided by the present disclosure includes two clamping pieces 1, a fixed mount 2, a ball head pull rod 4, a plastic sleeve 5 and a steel sleeve 6.

The two clamping pieces 1 are disposed at a front end of the fixed mount 2 through a fixing pin 3, and the two clamping pieces 1 are oppositely disposed. The fixing pin 3 respectively passes through sliding slots 13 disposed in the middle of the two clamping pieces 1 and limits the two clamping pieces 1 between two brackets at the front end of the fixed mount 2. The fixing pin 3 may slide along the sliding slots 13, and the two clamping pieces 1 may rotate around the fixing pin 3. Rear ends of the two clamping pieces 2 are respectively provided with a hemispherical shell-shaped connecting portion 18 (also referred to as a ball head bowl). The ball head pull rod 4 includes a pull rod 41 and a ball head 40 disposed at a front end of the pull rod 41, and the ball head 40 of the ball head pull rod 4 is limited to the inside of the two oppositely disposed hemispherical shell-shaped connecting portions 18. The ball head pull rod 4 is configured to drive opening and closing of the two clamping pieces 1. As the ball head 40 reciprocates in an up-down direction, the rear ends of the two clamping pieces 1 are driven to reciprocate in the up-down direction, and at the same time, under the action of the fixing pin 3, the two clamping pieces 1 are opened and closed. After the two clamping pieces 1 are closed, by continuing pulling the ball head pull rod 4 rearward, the two closed clamping pieces 1 are stuck at the front end of the fixed mount 2. Then, by continuing pulling the ball head pull rod 4 rearward, the ball head 40 moves rearward to deform the hemispherical shell-shaped connecting portions 18, and the ball head 40 is separated from the hemispherical shell-shaped connecting portions 18.

The fixed mount 2 includes a tube body 21 and two brackets 22 disposed at a front end of the tube body 21. The tube body 21 includes a plurality of stepped cavities, and an inner diameter of an upper cavity is less than an inner diameter of a lower cavity. The plastic sleeve 5 and the steel sleeve 6 are disposed in a region of a lower portion of an inner cavity of the fixed mount 2 with the greatest inner diameter (that is, disposed in the bottommost cavity), and the plastic sleeve 5 is disposed between the steel sleeve 6 and an inner wall of the fixed mount 2. The ball head pull rod 4 passes through the steel sleeve 6. After the ball head pull rod 4 is separated from the clamping pieces 1, by pulling the ball head pull rod 4 rearward, the ball head 40 drives the steel sleeve 6 to slide out of the plastic sleeve 5.

Figure 3:
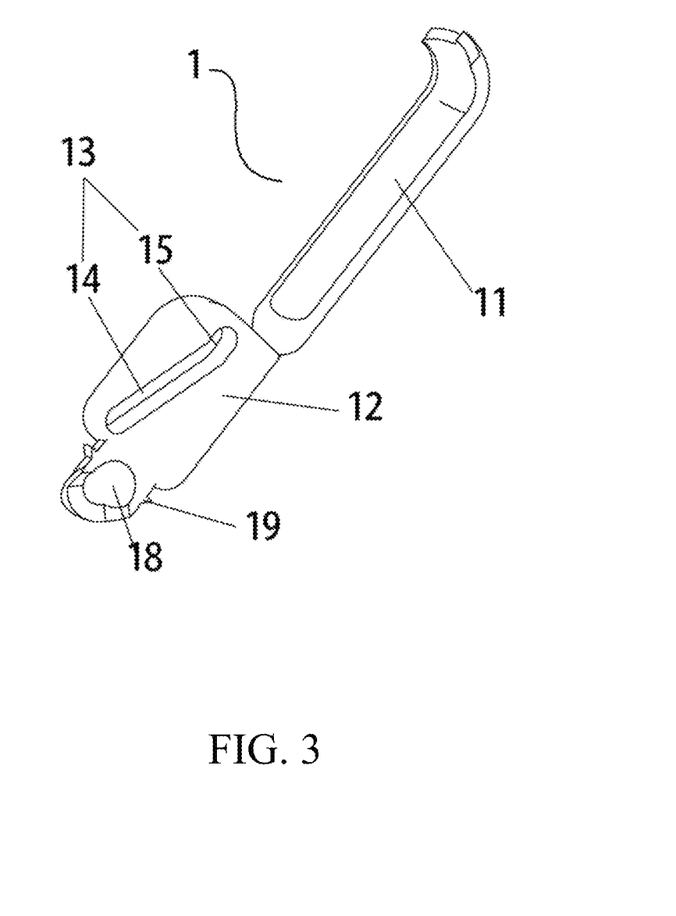
FIG. 3 is a schematic structural diagram of a clamping piece in the hemostatic clamp.
Figure 5:
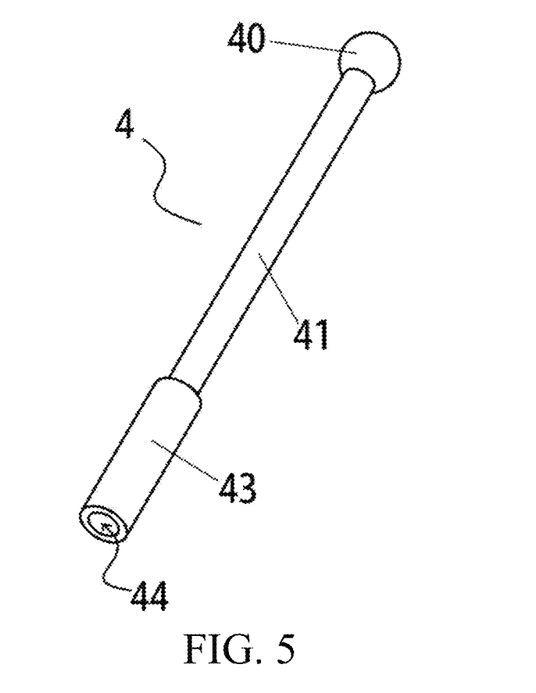
FIG. 5 is a schematic structural diagram of a ball head pull rod in the hemostatic clamp.

Specifically, as shown in FIG. 3, the clamping piece 1 is provided with an inwardly closed jaw 11 at the front, a middle connecting body 12 at the middle and the hemispherical shell-shaped connecting portion 18 at the rear end. Serrations extending in a closing direction are formed at a front end of the jaw 11 and configured to realize clamping. The sliding slot 13 is formed in the middle connecting body 12 of the clamping piece 1. The sliding slot 13 includes an inclined portion 14 and a bent portion 15. A distance between the inclined portion 14 and an outer wall of the clamping piece 1 gradually decreases from the rear end to a front end of the clamping piece 1, and the outer wall of the clamping piece 1 refers to a side wall facing away from the closing direction of the clamping piece 1. The bent portion 15 is disposed at one end of the sliding slot 13 away from the hemispherical shell-shaped connecting portion 18, that is, disposed at a position near the front end of the clamping piece 1, and an extending direction of the bent portion 15 is parallel to a length direction of the clamping piece 1. When the fixing pin 3 slides from the inclined portion 14 of the sliding slot 13 to a position of the bent portion 15, the two clamping pieces 1 are in a closed locking position. The hemispherical shell-shaped connecting portions 18 of the two clamping pieces 1 have opposite and facing opening directions to limit the ball head 40 of the ball head pull rod 4 to the inside of the two hemispherical shell-shaped connecting portions 18. A structure of the ball head pull rod 4 is shown in FIG. 5. The ball head pull rod 4 includes the pull rod 41 and the ball head 40 disposed at the front end of the pull rod 41. A notch is formed in each of the hemispherical shell-shaped connecting portions 18 and configured to accommodate the pull rod 41 of the ball head pull rod 4. By pulling the ball head pull rod 4, the ball head 40 moves rearward to deform the hemispherical shell-shaped connecting portions 18, and the ball head pull rod 4 is separated from the hemispherical shell-shaped connecting portions 18.

Besides, an annular protrusion 19 is formed on an outer wall of the hemispherical shell-shaped connecting portion 18 and configured to fit with an annular flange 20 disposed at the front end of the tube body of the fixed mount 2. When the hemispherical shell-shaped connecting portion 18 moves rearward to the inside of the fixed mount 2, the protrusion 19 is stuck at the rear of the annular flange 20 to realize closed locking. In order to facilitate pulling the ball head pull rod 4, the protrusion 19 has an inclined transitional surface.

Figure 4:
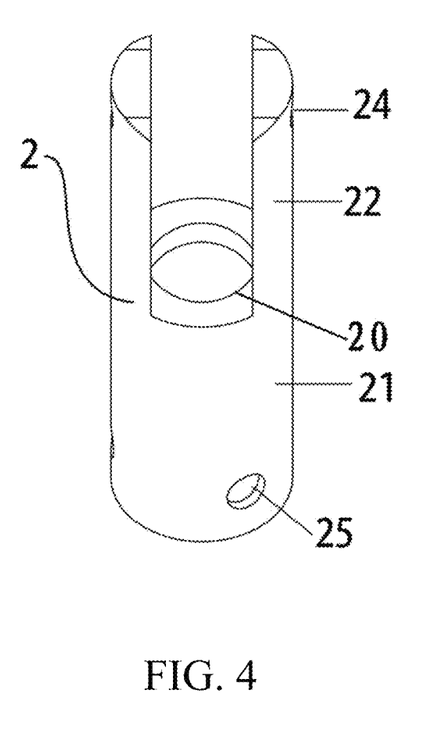
FIG. 4 is a schematic structural diagram of a fixed mount in the hemostatic clamp.
Figure 4A:
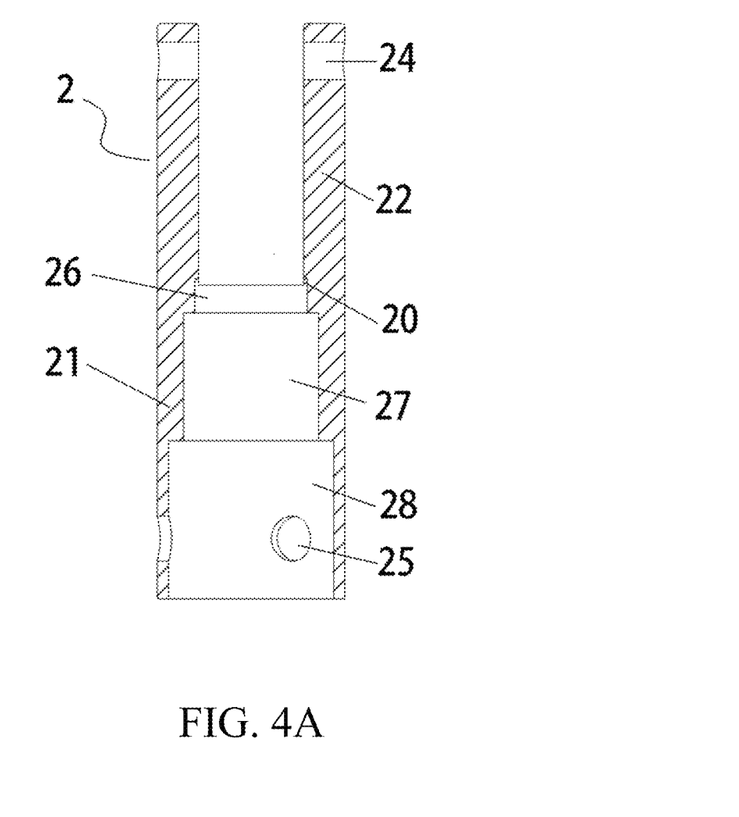
FIG. 4A is a schematic cross-sectional view of the fixed mount shown in FIG. 4.

As shown in FIG. 4 and FIG. 4A, the fixed mount 2 includes the tube body 21 and the two brackets 22 disposed at the front end of the tube body 21, and the two brackets 22 respectively extend upward from two opposite sides of the tube body 21 independently. Corresponding positions of upper portions of the two brackets 22 are respectively provided with a through hole 24. The fixing pin 3 respectively passes through the sliding slots 13 disposed in the middle of the two clamping pieces 1, and two ends of the fixing pin are respectively fixed after passing through the through holes 24, thereby limiting the two clamping pieces 1 between the two brackets 22 at the front end of the fixed mount 2. The clamping pieces 1 may be opened and closed in a region between the two brackets 22.

As shown in FIG. 2 and FIG. 4A, the plurality of stepped cavities is formed in the tube body 21, and the inner diameter of the upper cavity is less than the inner diameter of the lower cavity. Since the inner diameter of the topmost cavity is less than a distance between the two brackets 22, one annular flange 20 is formed at a position where the topmost cavity meets the bracket, and thus, the annular flange 20 defines a narrow inlet of the tube body 21. Under the action of the ball head pull rod 4, the hemispherical shell-shaped connecting portions 18 of the two clamping pieces 1 enter the topmost cavity 26 through the above narrow inlet, so that the protrusions 19 disposed on the outer walls of the hemispherical shell-shaped connecting portions 18 are stuck at a lower portion of the annular flange 20 to realize closed locking.

In the illustrated embodiment, inside the tube body 21, two stepped regions with a smaller top and a larger bottom are also formed below the topmost cavity, and an inner diameter of an upper first region 27 is less than an inner diameter of a lower second region 28. The plastic sleeve 5 and the steel sleeve 6 are disposed at the inside of the second region 28. Besides, by forming three holes 25 in circumference of the second region 28 and by injecting glue into the tube body 21 of the fixed mount 2 through the holes 25, the fixed mount 2 is bonded to the plastic sleeve 5.

The structure of the ball head pull rod 4 is shown in FIG. 5. The ball head pull rod 4 includes the pull rod 41 and the ball head 40 disposed at the front end of the pull rod 41, and a diameter of the ball head 40 is greater than a diameter of the pull rod 41.

The ball head 40 is limited to the inside of the hemispherical shell-shaped connecting portions 18 at the rear ends of the two clamping pieces 1. Reciprocating motion of the ball head 40 forms reciprocating motion of the clamping pieces 1, and at the same time, under the action of the fixing pin 3, the two clamping pieces 1 are opened and closed. After the two clamping pieces 1 are closed, the ball head 40 continues moving rearward such that the two clamping pieces 1 are stuck at the inside of the fixed mount 2 and then the hemispherical shell-shaped connecting portions 18 at the rear ends of the two clamping pieces 1 are deformed, thereby realizing separation of the ball head 40 from the hemispherical shell-shaped connecting portions 18.

The diameter of the pull rod 41 is equal to or slightly smaller than an inner diameter of the steel sleeve 6, so that the pull rod 41 stably moves up and down along a hole in the steel sleeve 6. The diameter of the ball head 40 is greater than the inner diameter of the steel sleeve 6, and therefore, when the ball head 40 continues moving rearward after moving to a position in contact with the steel sleeve 6, the ball head 40 drives the steel sleeve 6 to slide out of the plastic sleeve 5.

The ball head pull rod 4 also includes a connecting tube 43. A top of the connecting tube 43 is connected to the pull rod 41. A bottom of the connecting tube 43 is configured to be connected to a pull rope. Specifically, a lower end of the pull rod 41 is inserted into the connecting tube 43 and fixed, and the pull rope is inserted into a hole 44 at the bottom of the connecting tube 43 and fixed, so that the ball head pull rod 4 is connected to the pull rope.

Figure 6:
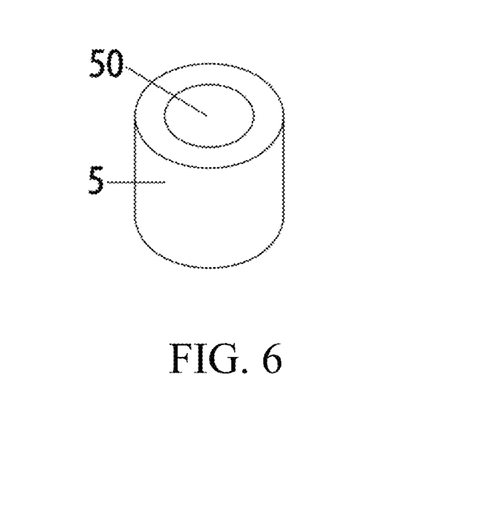
FIG. 6 is a schematic structural diagram of a plastic sleeve in the hemostatic clamp.
Figure 7:
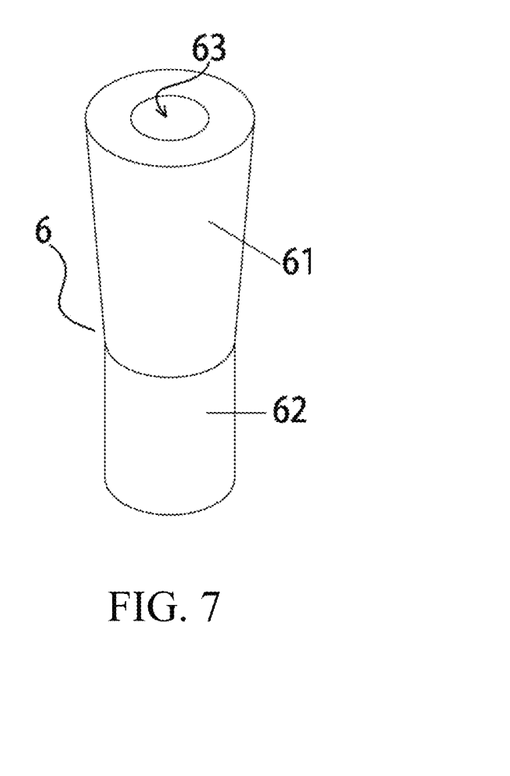
FIG. 7 is a schematic structural diagram of a steel sleeve in the hemostatic clamp.
Figure 8:
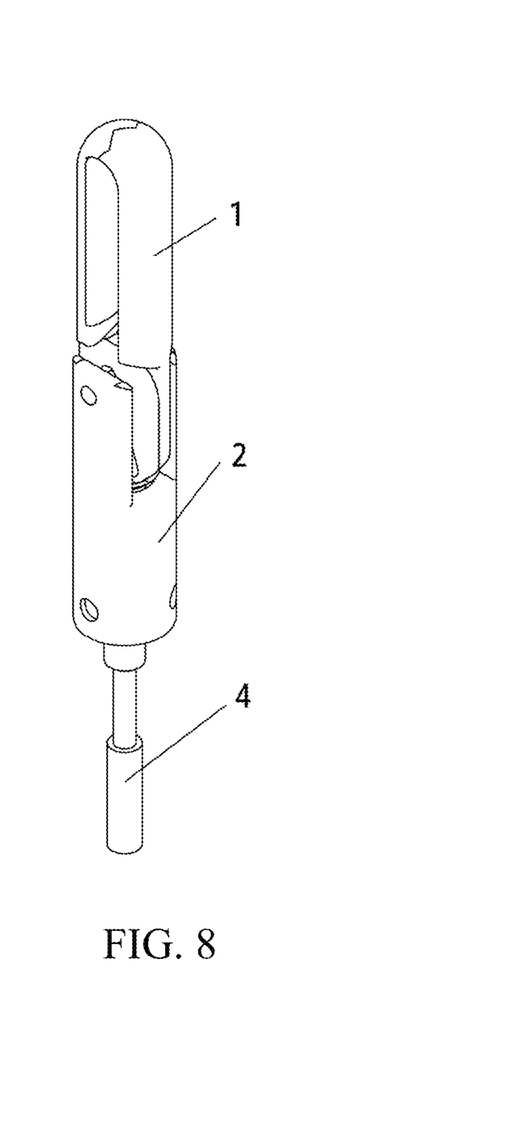
FIG. 8 is a schematic diagram of the hemostatic clamp shown in FIG. 1 in a closed state.
Figure 9:
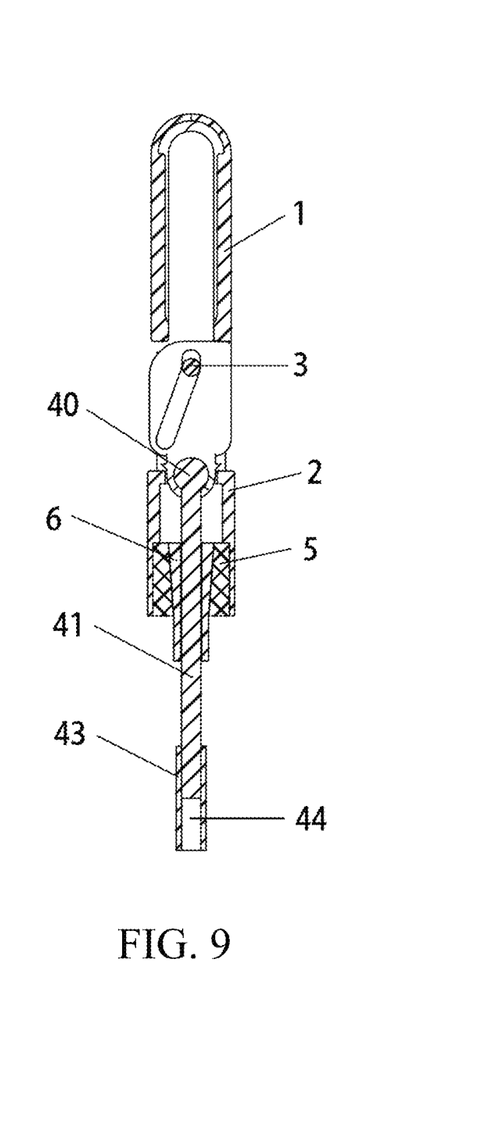
FIG. 9 is a schematic cross-sectional view of the hemostatic clamp shown in FIG. 8.

Structures of the plastic sleeve 5 and the steel sleeve 6 are as shown in FIGS. 6 and 7. An outer diameter of the plastic sleeve 5 matches an inner diameter of the bottommost region (that is, the second region 28) of the fixed mount 2. A size of an inner surface of the plastic sleeve 5 matches a size of an outer surface of the steel sleeve 6 at a portion fitting therewith.

As shown in FIG. 2 and FIG. 6, the inner surface 50 of the plastic sleeve 5 is an inclined conical surface. An inner diameter of a top of the plastic sleeve 5 is greater than an inner diameter of a bottom of the plastic sleeve 5.

As shown in FIG. 7, the steel sleeve 6 is divided into upper and lower portions. The upper portion 61 is configured to match the plastic sleeve 5, and the lower portion 62 is configured to connect a spring tube. Specifically, an outer surface of the upper portion 61 is a conical surface matching the inner surface 50 of the plastic sleeve 5, and the outer surface of the upper portion 61 may form an interference fit with the inner surface of the plastic sleeve 5. An outer surface of the lower portion 62 is a cylindrical surface, and may be inserted into the spring tube and fixed.

In the above structure, the plastic sleeve 5 and the steel sleeve 6 are disposed in the bottom cavity of the fixed mount 2, and by pulling the ball head pull rod 4 rearward, the ball head 40 of the ball head pull rod 4 pushes the steel sleeve 6 to squeeze the plastic sleeve 5 to deform, so that the ball head pull rod 4 drives the steel sleeve 6 to slide out of the plastic sleeve 5, thereby realizing separation of the control portion, which includes the ball head pull rod 4, the steel sleeve 6, and the spring tube and a control grip connected with the steel sleeve 6, from the clamping portion at the front end of the hemostatic clamp. The clamping portion left in the body, including the two clamping pieces 1, the fixed mount 2, the fixing pin 3 and the plastic sleeve 5, may be made of some degradable material.

A structure of the hemostatic clamp provided by the present disclosure has been described above, and an assembly process and a use process of the hemostatic clamp will be described in detail below with reference to FIGS. 1, 2, 8, 9 and 10.

When the hemostatic clamp is assembled, firstly, the ball head 40 of the ball head pull rod 4 is placed in the hemispherical shell-shaped connecting portions 18 of the two clamping pieces 1. The fixed mount 2 is sleeved over the two clamping pieces 1, and the fixing pin 3 is inserted. A sheath cap may be sleeved over the outside of the fixing pin 3 to prevent the fixing pin 3 from coming off. Then, the plastic sleeve 5 and the steel sleeve 6 are sleeved over the pull rod 41 of the ball head pull rod 4. The plastic sleeve 5 is inserted into a base of the fixed mount 2. In order to enhance connection strength between the fixed mount 2 and the plastic sleeve 5, the glue is dispensed at the three circular holes 25 reserved in the fixed mount 2 such that the plastic sleeve 5 and the fixed mount 2 are bonded together. Next, the ball head pull rod 4 is connected with the connecting tube 43 and then the connecting tube 43 is connected with the pull rope. Finally, a thin end of the steel sleeve 6 is inserted into an inner hole of the spring tube and welded with the spring tube together, and a grip component is mounted.

The above hemostatic clamp clamps a target affected part by closing the two symmetrical clamping pieces 1 to achieve the effects of stopping bleeding and closing a wound. Opened and closed states of the hemostatic clamp during tentative operation are respectively as shown in FIG. 1, FIG. 2, FIG. 8 and FIG. 9. When the ball head pull rod 4 is pushed forward, the two clamping pieces 1 are opened under the action of the fixing pin 3 and the ball head 40. When the ball head pull rod 4 is pulled rearward, the two clamping pieces 1 are closed under the action of the fixing pin 3 and the ball head 40. As the ball head pull rod 4 reciprocates, the clamping pieces 1 may be opened and closed many times. In this process, the fixing pin 3 slides in the inclined portions 14 of the sliding slots 13 of the two clamping pieces 1, and the hemispherical shell-shaped connecting portions 18 of the clamping pieces 1 move up and down between two branches of the fixed mount 2.

Figure 10:
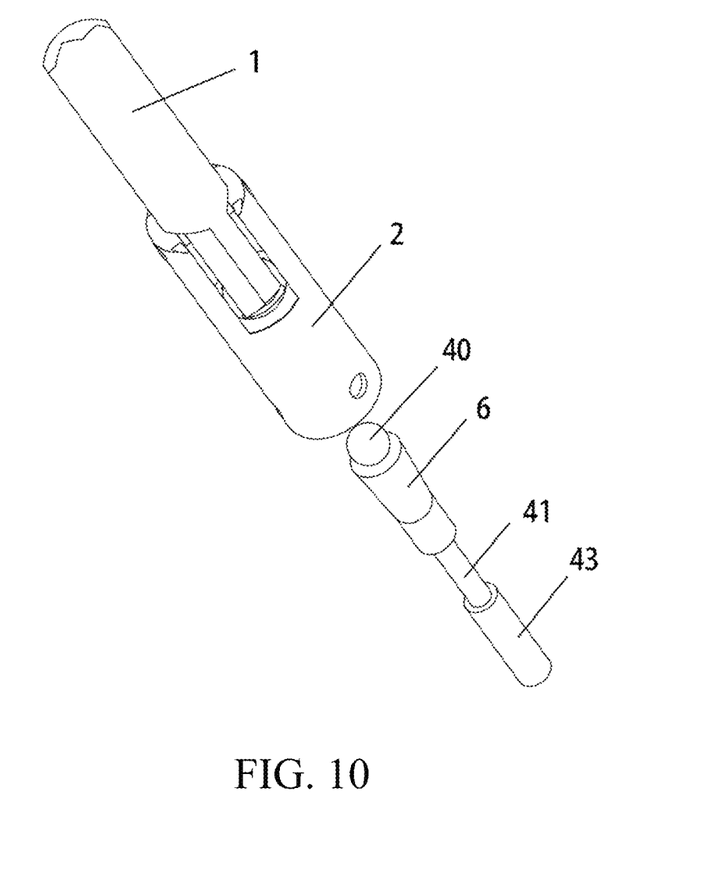
FIG. 10 is a schematic diagram of the hemostatic clamp shown in FIG. 1 in a separated state.

As shown in FIG. 10, when the hemostatic clamp clamps a target tissue, by pulling the ball head pull rod 4 rearward, the hemispherical shell-shaped connecting portions 18 move rearward. When the protrusions 19 on the outside of the hemispherical shell-shaped connecting portions 18 are stuck at the rear of the annular flange 20 of the topmost cavity 26 of the fixed mount 2, the two clamping pieces 1 are in the closed locking position. At the same time, the fixing pin 3 slides into the bent portions 15 of the sliding slots 13 to realize synchronous locking.

By continuing pulling the ball head pull rod 4 rearward, the ball head 40 deforms the hemispherical shell-shaped connecting portions 18, and the ball head 40 is separated from the hemispherical shell-shaped connecting portions 18. By continuing pulling the ball head pull rod 4 rearward, the ball head 40 drives the steel sleeve 6 to force the plastic sleeve 5 to deform and to slide out of the plastic sleeve 5, thereby realizing the separation of the clamping portion at the front end of the hemostatic clamp from the control portion at the rear end. Then, by pulling the pull rope rearward, the ball head pull rod 4, the steel sleeve 6, the spring tube and the like move rearward together.

The structure of the hemostatic clamp provided by the present disclosure and the tentative operation, closed locking and separation processes thereof are described in detail above. After the fixed mount 2, the plastic sleeve 5 and the steel sleeve 6 of the hemostatic clamp are separated, the fixed mount 2, the clamping pieces 1, the fixing pin 3 and the plastic sleeve 5 are left in a human digestive tract. In order to facilitate elimination from the body, part or all of the fixed mount 2, the clamping pieces 1, the fixing pin 3 and the plastic sleeve 5 are recommended to be made of some degradable biological material, so that during hemostasis of the hemostatic clamp, the above components can be gradually decomposed and finally completely eliminated from the human body.

Based on the above, according to the hemostatic clamp provided by the present disclosure, the two clamping pieces are opened and closed through the ball head pull rod, and the clamping portion at the front end and the control portion at the rear end are separated through fit of the ball head pull rod with the plastic sleeve and the steel sleeve. Therefore, the hemostatic clamp has the advantages of simple structure, simple operation and high operation stability and is a hemostatic clamp suitable for wide use.

The hemostatic clamp provided in the present disclosure has been described in detail above. Any obvious modification made by those of ordinary skill in the art to the present disclosure without departing from the essential of the present disclosure will constitute an infringement of the patent right of the present disclosure, and those of ordinary skill who make such modification shall bear corresponding legal liabilities.

What is claimed is:

1. A system comprising a hemostatic clamp, comprising a fixed mount, two clamping pieces and a ball head pull rod, the two clamping pieces being oppositely disposed at a front end of the fixed mount, the ball head pull rod comprises a pull rod and a ball head disposed at a front end of the pull rod, and the ball head pull rod being configured to drive opening and closing of the two clamping pieces, wherein
the hemostatic clamp also comprises a plastic sleeve and a steel sleeve, the plastic sleeve and the steel sleeve are disposed on a lower portion of an inner cavity of the fixed mount, the plastic sleeve being disposed between the steel sleeve and an inner wall of the fixed mount;
the ball head pull rod passes through the steel sleeve; and
wherein the ball head pull rod is configured to be separated from the clamping pieces by pulling the ball head pull rod rearward, and after the ball head pull rod is separated from the clamping pieces, the ball head is configured to drive the steel sleeve to slide out of the plastic sleeve.

2. The system according to claim 1, wherein
an inner surface of the plastic sleeve is an inclined conical surface, and an inner diameter of a top of the plastic sleeve is greater than an inner diameter of a bottom of the plastic sleeve; and a size of the inner surface of the plastic sleeve matches a size of an outer surface of the steel sleeve at a portion fitting therewith.

3. The system according to claim 1, wherein
the steel sleeve is divided into upper and lower portions, wherein the upper portion is configured to match the plastic sleeve, and the lower portion is configured to connect a spring tube.

4. The system according to claim 3, wherein
an outer surface of the upper portion of the steel sleeve forms an interference fit with an inner surface of the plastic sleeve.

5. The system according to claim 1, wherein
a plurality of holes is disposed in circumference of the fixed mount, and the plastic sleeve is bonded to the fixed mount by injecting glue into the fixed mount through the holes.

6. The system according to claim 1, wherein
a diameter of the ball head is greater than a diameter of the pull rod, and the diameter of the ball head is greater than an inner diameter of the steel sleeve; and the diameter of the pull rod is equal to the inner diameter of the steel sleeve.

7. The system according to claim 6, wherein
the ball head pull rod also comprises a connecting tube, a top of the connecting tube being connected to the pull rod, and a bottom of the connecting tube being configured to be connected to a pull rope.

8. The system according to claim 1, wherein
the fixed mount comprises a tube body and two brackets disposed at a front end of the tube body, the two brackets respectively extending upward from two opposite sides of the tube body independently; and the two clamping pieces are disposed between the two brackets at the front end of the fixed mount through a fixing pin.

9. The system according to claim 8, wherein
the tube body comprises a plurality of stepped cavities, wherein an inner diameter of an upper cavity is less than an inner diameter of a lower cavity; and the plastic sleeve and the steel sleeve are disposed inside the bottommost cavity.

10. The system according to claim 9, wherein
one annular flange is formed at a position where the topmost cavity meets one of the brackets.

11. The system according to claim 1, wherein
rear ends of the two clamping pieces are respectively provided with a hemispherical shell-shaped connecting portion; the ball head is limited to the inside of the two hemispherical shell-shaped connecting portions; and
the ball head is configured to moves rearward to deform the hemispherical shell-shaped connecting portions, and the ball head is configured to be separated from the hemispherical shell-shaped connecting portions.

12. The system according to claim 11, wherein
a protrusion is formed on an outer wall of the hemispherical shell-shaped connecting portion and configured to fit with an annular flange disposed on the fixed mount such that the clamping pieces are in a closed locking position.

13. The system according to claim 1, wherein
a fixing pin respectively passes through sliding slots disposed in the middle of the two clamping pieces and limits the two clamping pieces between two brackets at the front end of the fixed mount.

14. The system according to claim 13, wherein
each of the sliding slots comprises an inclined portion and a bent portion, wherein the bent portion is disposed at a position near front ends of the two clamping pieces, and when the fixing pin moves into the bent portion, the two clamping pieces are in a closed locking position.

15. The system according to claim 14, wherein
a distance between the inclined portion and an outer wall of each of the two clamping pieces gradually decreases from a rear end to the front end of the each of the two clamping pieces; and an extending direction of the bent portion is parallel to a length direction of the each of the two clamping pieces.

\* \* \* \* \*